(12) United States Patent
Madurkay

(10) Patent No.: US 6,317,886 B1
(45) Date of Patent: Nov. 20, 2001

(54) WELDING MASK WITH SLATTED WINDOW

(76) Inventor: Esteban Madurkay, 9125 Nagel Dr., Thornton, CO (US) 80229

( * ) Notice: Subject to any disclaimer, the term of this patent is extended or adjusted under 35 U.S.C. 154(b) by 0 days.

(21) Appl. No.: 09/568,534

(22) Filed: May 9, 2000

(51) Int. Cl.[7] .................................................. A61F 9/06
(52) U.S. Cl. .................................................. 2/8; 2/11; 2/433
(58) Field of Search .................................. 2/8, 432, 424, 2/9, 10, 13, 433, 11; 219/147

(56) References Cited

U.S. PATENT DOCUMENTS

| | | | |
|---|---|---|---|
| 2,105,018 | * | 1/1938 | Tatter ........................................... 2/8 |
| 4,130,903 | * | 12/1978 | Van den Berg et al. ..................... 2/8 |
| 4,945,572 | * | 8/1990 | Rosen .......................................... 2/8 |
| 4,953,231 | * | 9/1990 | Burnett ................................. 2/433 X |

* cited by examiner

*Primary Examiner*—Peter Nerbun
(74) *Attorney, Agent, or Firm*—Ramon L. Pizzarro; Edwin H. Crabtree

(57) ABSTRACT

A mask for covering a person's face while welding. The mask includes a body adapted for covering the person's face, the body having a window with a translucent lens positioned over the window. The lens include at least one translucent slat, each slat having a first end and a second end. The first end of each slat being pivotally supported against the body of the mask and movable from a first position where each slat covers a projected area over the body to a second position where each slat covers a reduced projected area over the body, so that part of the face is exposed when the slats are in the second position.

8 Claims, 3 Drawing Sheets

WELDING MASK WITH SLATTED WINDOW

BACKGROUND OF THE INVENTION (a). Field of the Invention

This invention generally relates to a mask used for protecting a welder's eyes from light and materials sprayed while arc welding. More particularly, and not by way of limitation, to a welder's mask with a shaded lens portion that is made of slatted lens sections that are movable by the user.

(b). Discussion of Known Art

In the field of arc welding, the welder is required to wear eye and face protection to protect the welder from the intense light given off from the arc, and from flying debris given off while welding, such as bits of molten metal. A burdensome drawback to these masks, however, has been the fact that the lens used for eye protection must be extremely obscure. The obscurity of the lens prevents the wearer from seeing through the lens while not welding, requiring that the user remove the mask in order to better inspect the work piece or simply look around the work area.

The problem of allowing the worker to see through the lens when not welding has been approached in several different ways. One approach has been to provide a lens with means that are sensitive to the intense light given off by the welding operation. These masks offer important advantages in that they allow the user to keep the mask on between episodes of welding. Thus, the user can weld, inspect the weld, and continue welding without having to change positions or rearrange his equipment in order to continue welding.

Other approaches at the problem of allowing the user to view the workpiece between welds include the provision of a hinged head support, which allows lifting of the entire mask over the user's head. These devices, however, are cumbersome and are difficult to keep in place while lifted.

Thus, there remains a need for an inexpensive, reliable device that allows the user to view the workpiece between episodes of welding. Furthermore, there remains a need for a welder's mask which will allow the user to view the workpiece without having to lift the entire mask off of his face.

There remains a need for a welder's face mask that can be actuated quickly to provide the welder with nearly instantaneous protection for his vision while welding.

Still further, there remains a need for a welding mask that can be easily automated to provide with an inexpensive automated shading system for a welder's mask.

SUMMARY

It has been discovered that the problems left unanswered by known art can be solved by providing a welder's mask that includes a darkened lens portion made from several segments or slats mounted next to one another. The ends of each slat is pivotally mounted to allow pivoting of the slats from a closed position to an opened position in a manner that is similar to the operation of a Venetian blind.

According to one embodiment of the invention the slats of darkened lens material are connected to one another by a linkage mechanism that allows simultaneous pivoting of all of the slats between the open and closed position. The activation of this linkage mechanism may be accomplished through the use of a hand operated mechanism that includes a push-button that is mounted on a support mask-support handle. The push-button is accessible to the user while he holds the mask over his face, so that the user may simply squeeze the button to pivot the slats. Pivoting the slats will bypass the darkened lens and allow the user to see through the mask. Thus, the user will be able to inspect the work piece in between welding sessions by simply pressing the button.

Alternatively, it is contemplated that the disclosed slat system may be electrically actuated by incorporating a solenoid, stepping motor, or the like to the linkage which actuates or pivots the slats. This arrangement, although more expensive than other highly preferred embodiments of the invention, will allow the actuation or operation of the slats by providing an electrical connection to the welding electrode mechanism. Thus, the presence of a current or the pressing of a trigger or button to actuate current to the electrode will activate the solenoid and close the slats of the lens. Of course, it is contemplated that a delay mechanism may be incorporated into this system to provide a slight delay between the squeezing of the trigger that actuates the current to the electrode and the actual activation of the circuitry that allows current to flow to the electrode. This will provide time for the slats to close fully before allowing the electrodes to produce a spark or light from welding.

It should also be understood that while the above and other advantages and results of the present invention will become apparent to those skilled in the art from the following detailed description and accompanying drawings, showing the contemplated novel construction, combinations and elements as herein described, and more particularly defined by the appended claims, it should be clearly understood that changes in the precise embodiments of the herein disclosed invention are meant to be included within the scope of the claims, except insofar as they may be precluded by the prior art.

DRAWINGS

The accompanying drawings illustrate preferred embodiments of the present invention according to the best mode presently devised for making and using the instant invention, and in which:

FIG. 4 is a schematic illustrating a circuit which may be used to activate the vanes by way of a solenoid or the like.

DETAILED DESCRIPTION OF PREFERRED EXEMPLAR EMBODIMENTS

While the invention will be described and disclosed here in connection with certain preferred embodiments, the description is not intended to limit the invention to the specific embodiments shown and described here, but rather the invention is intended to cover all alternative embodiments and modifications that fall within the spirit and scope of the invention as defined by the claims included herein as well as any equivalents of the disclosed and claimed invention.

Figure 1:
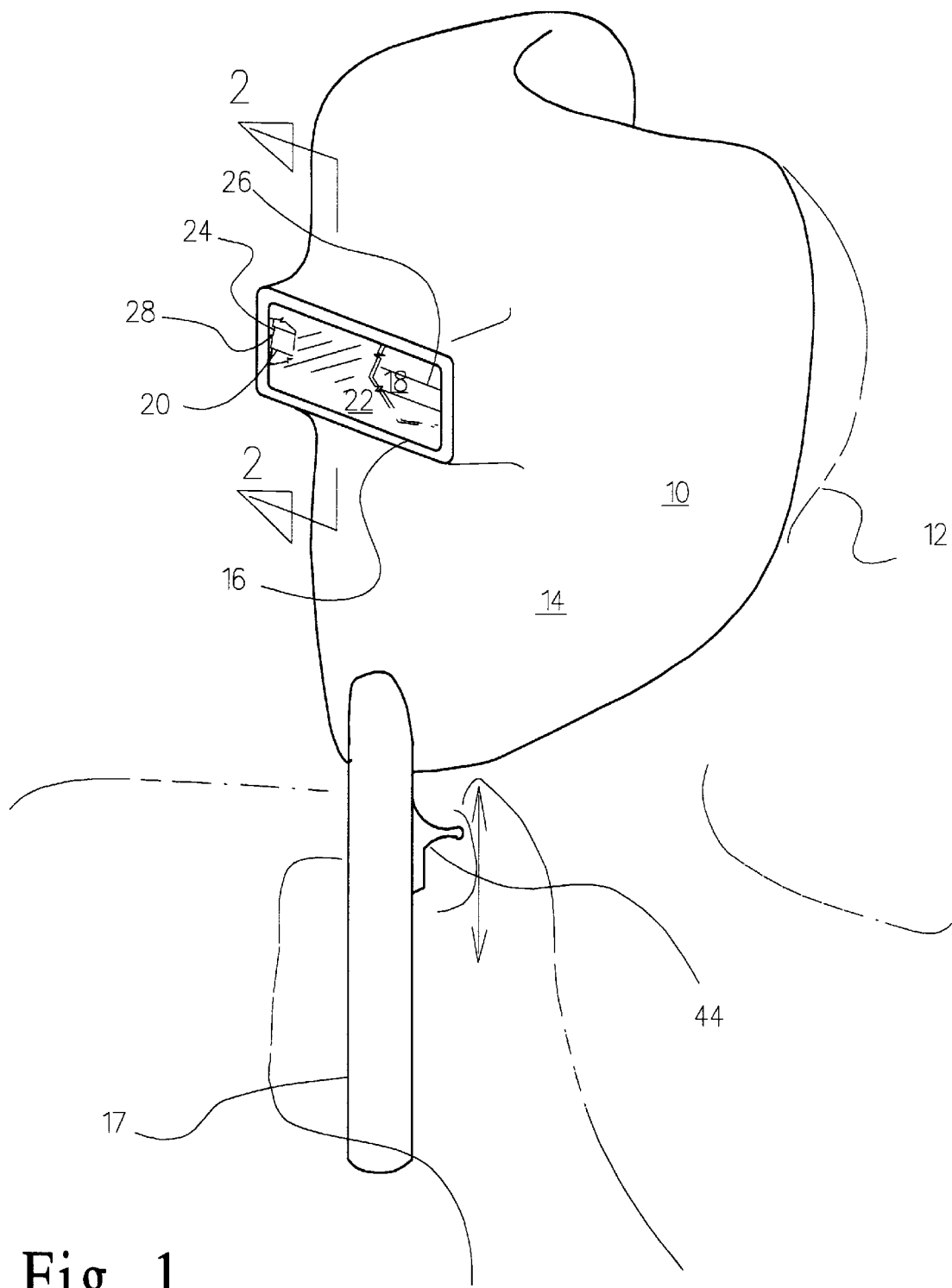
FIG. 1 is a perspective view of an embodiment of the invention in use over a person's face.

Turning now to FIG. 1 where a mask 10 for covering a person's face or head 12 while welding has been illustrated in use. Much of the illustrated mask 10 includes components that are widely used in welding masks. For example, the mask 10 includes a body 14 which has been adapted for covering the person's face. The body 14 is made of an opaque material, such as an opaque plastic composite material, or any other suitable material. The mask 10 of a highly preferred embodiment of the invention includes a handle 17, or means adapted for supporting the mask over the person's face, that allows the user to hold the mask 10 in close proximity over his face while welding. It is important to note that while embodiments discussed herein are particularly well suited for use in a mask with a handle 17, it is contemplated that these mechanisms may be installed in masks without handles, provided that a suitable actuation mechanism be provided.

As illustrated in FIG. 1, the body 14 includes a window 16 opening that allows the user to peer through the mask to view the work piece. The window 16 will include a translucent lens 18 that covers the window 16. In a highly preferred embodiment of the invention, the lens 18 is made up of at least one translucent slat 20 that is pivotally mounted across the window opening. In the illustrated example, the slat 20 is protected or concealed by a fixed protective lens 22 that extends across the window 16 to protect the lens 18 that is constructed from at least one pivotable slat 20.

Each slat 20 will include a first end 24 and a second end 26. The first end 24 of each slat 20 will include means for pivotally supporting the slat 20 against the body 14 of the mask 10. In a highly preferred embodiment of the invention these means for pivotally supporting the slat includes a pinned support 28 which supports the slat 20 allows the slat to be moved.

Figures 2, 3:
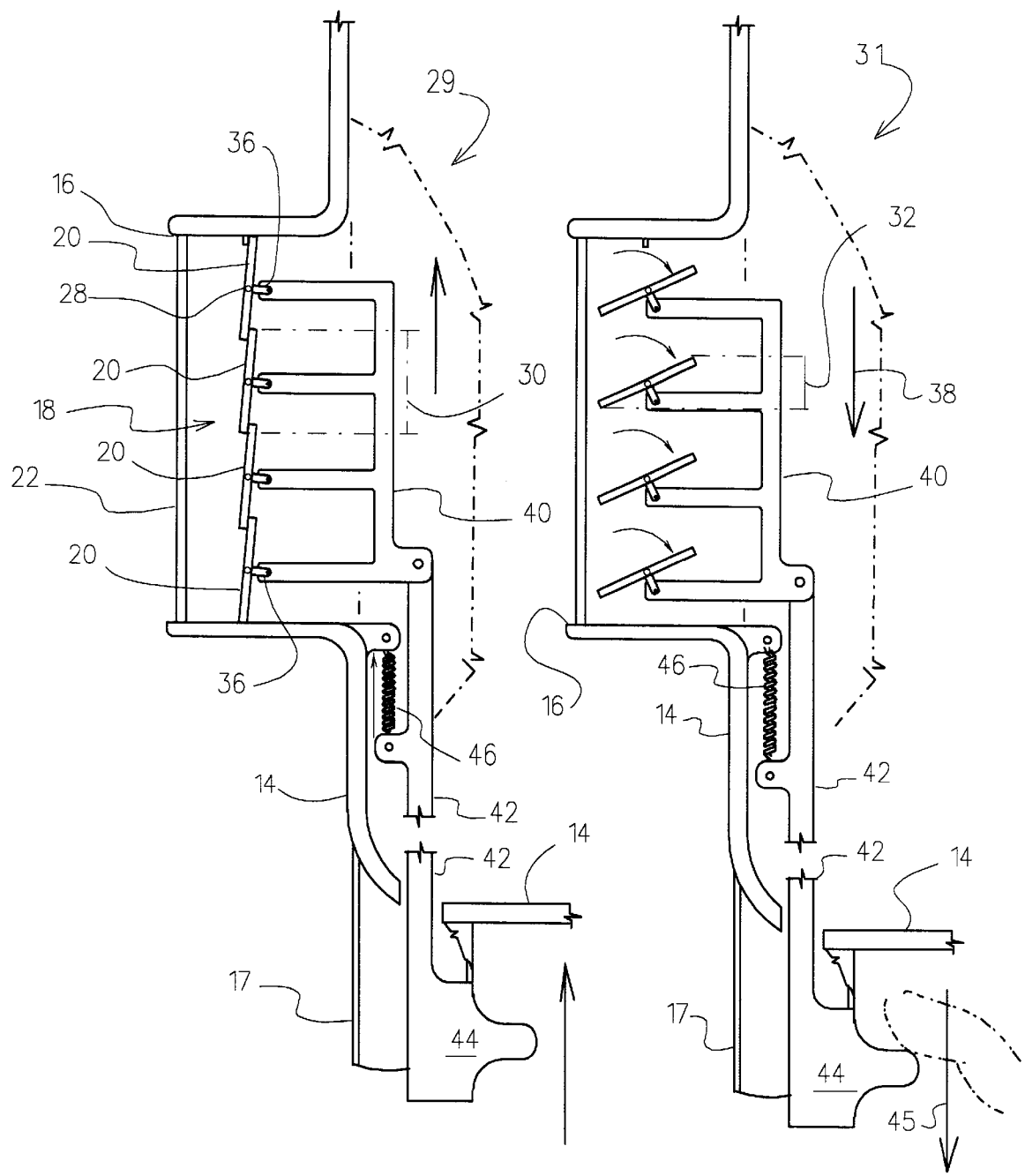
FIG. 2 is a sectional view taken from FIG. 1 and illustrating a preferred embodiment of the linkage mechanism while the lens is in the closed position, protecting the wearer.
FIG. 3 is a sectional view taken from FIG. 1 and illustrates the movement of the linkage to open the slats of the lens to allow the user to see through the mask under daylight conditions.

Referring now to FIGS. 2 and 3, where a section taken in the direction indicated by the section arrows of FIG. 1 has been illustrated. FIGS. 2 and 3 illustrate that the slat 20, or multiple slats 20 as used in the illustrated preferred embodiment, will be movable from a first position 29, illustrated in FIG. 1, where each slat covers a projected area 30 over the body or head 12 of the user to a second position 31, illustrated in FIG. 3, wherein the slat 20 covers a reduced projected area 32 over the body or head 12 of the user.

In order to move the slats from the first position 29 to the second position 31, a linkage mechanism, or means for pivoting each slat 20, has been incorporated into the mask 10. The means for pivoting will preferably include a lever 36 that will cause the slat to pivot to the second position 31 when pulled in the general direction of arrow 38. The lever 36 of each slat 20 is connected to drag link 40 that is used to move or pivot all of the slats 20 simultaneously.

The drag link 40 is in turn attached to a connecting rod 42 that is actuated by a trigger 44. Thus, movements of the trigger 44 cause movements in the connecting rod 42, which in turn moves the drag link 40, causing the slats 20 to pivot about the pinned support 28. Movements of the trigger 44 in the direction of arrow 45 will cause extension of the return spring 46. The return spring 46 will pull trigger 44 back in the direction of arrow 47, causing the mechanism to move the slats 20 to the first position 29, closing the slats 20 or lens 18. Closing of the slats 20 will cover the entire window 16, allowing the lens 18 to filter out the harmful light given off by the welding operation.

Figure 4:
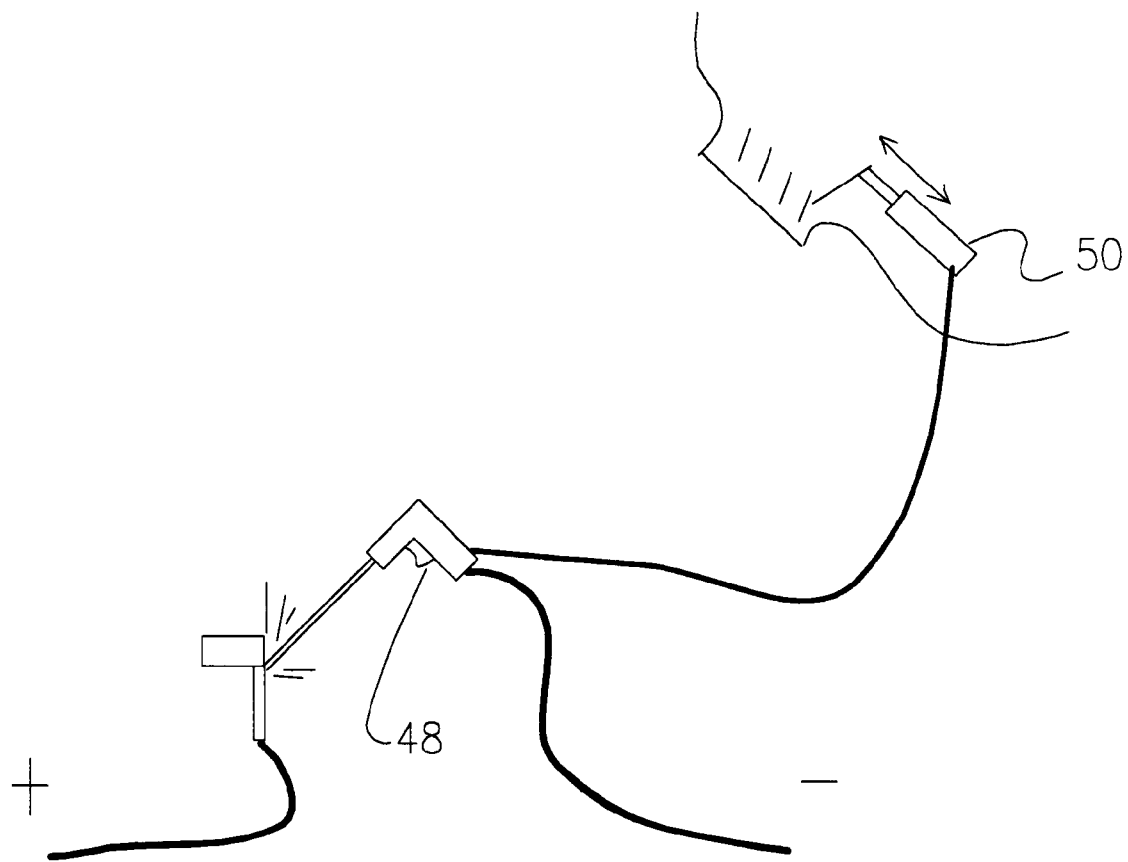

Referring now to FIG. 4, it will be understood that the disclosed invention may be electrically actuated by providing a switch 48 that is tripped by the squeezing of the switch used to activate the current for the welding operation. The switch 48 activates a solenoid 50 which is connected to the connecting rod 42. Therefore activation of the current for initiating the welding operation will cause the solenoid to give way to the return spring 46, closing the slats 20.

Thus it can be appreciated that the above described embodiments are illustrative of just a few of the numerous variations of arrangements of the disclosed elements used to carry out the disclosed invention. Moreover, while the invention has been particularly shown, described and illustrated in detail with reference to preferred embodiments and modifications thereof, it should be understood that the foregoing and other modifications are exemplary only, and that equivalent changes in form and detail may be made without departing from the true spirit and scope of the invention as claimed, except as precluded by the prior art.

What is claimed is:

1. A mask for covering a person's face while welding, the mask comprising:

a body adapted for covering the person's face, the body having a window and a handle positioned below the window;

a translucent lens positioned over said window, the lens comprising at least two translucent slats, each slat having a first end and a second end, the first end of each slat having means pivotally supporting the slat against the body of the mask and providing motion of each slat from a first position where each slat covers a projected area over the face to a second position wherein each slat covers a reduced projected area over the face; and a spring loaded trigger mechanism mounted from said handle, the trigger mechanism serving for simultaneously pivoting slats from the first position to the second position, so that when the mask is placed over the face the person, the slats cover part of the face when the slats are in the first position, and so that part of the face is exposed when the slats are in the second position, and so that the spring loaded trigger mechanism biases the slats to said first position.

2. A mask according to claim 1 wherein said means for pivoting each slat from the first position to the said slats are connected to one another by a link connecting at least two of said levers to said trigger, so that pivoting of the slats is accomplished by pulling on the trigger.

3. A mask for covering a person's face while welding, the mask comprising:

a body adapted for covering the person's face, the body having a window and a handle positioned next to the window;

a fixed protective lens and a translucent lens positioned over said window, the translucent lens being spaced from the fixed protective lens and comprising a plurality of translucent slats, each of the slats having a first end and a second end, the first end of each slat being behind the translucent lens and pivotally supported against the body of the mask;

a spring loaded trigger mechanism for providing motion of each slat from a first position where each slat covers a projected area over the face to a second position wherein the slats cover a reduced projected area over the face; and a spring loaded trigger mechanism mounted on said handle, the spring loaded trigger mechanism serving to pivot the slats from the first position to the second position, so that when the mask is placed over the face the person covers part of the face when the slats are in the first position, and so that part of the face is exposed when the slats are in the second position.

4. A mask according to claim 3 wherein each of said is pivotally connected to a lever connected to a link connected to the trigger mechanism.

5. A method for temporarily protecting a portion of a person's face while welding, the method comprising:

providing a mask for covering a person's face while welding, the mask comprising:

a body adapted for covering the person's face, the body having a window and a handle positioned below the window;

a fixed protective lens positioned across said window, and a translucent lens positioned over said window, behind the fixed protective lens, the translucent lens comprising a plurality of translucent slats, each of the slats having a first end and a second end, the first end of each slat being pivotally supported from said window; and a spring loaded trigger mechanism for pivoting the slats from the first position to the second position, and biasing the slats towards the first position; placing the mask over the face the person to cover at least part of the face when with the slats when the slats are in the first position; and exposing part of the face from behind the slats when the slats are in the second position.

6. A method according to claim 5 wherein the trigger mechanism includes a lever connected to the first end of each slat, and a link connecting at least two of said levers.

7. A method according to claim 6 wherein the link is connected to a hand movable trigger.

8. A method according to claim 7 wherein the link is connected to a solenoid.

* * * * *